United States Patent
Zeng et al.

(12) 
(10) Patent No.: US 6,593,576 B2
(45) Date of Patent: Jul. 15, 2003

(54) VARIABLE ANGULAR SAMPLING RATE FOR ROTATING SLAT-HOLE DETECTORS OF GAMMA CAMERAS

(75) Inventors: Gengsheng Lawrence Zeng, Sandy, UT (US); Daniel Gagnon, Twinsburg, OH (US)

(73) Assignee: Koninklijke Philips Electronics, N.V., Eindhoven (NL)

(*) Notice: Subject to any disclaimer, the term of this patent is extended or adjusted under 35 U.S.C. 154(b) by 50 days.

(21) Appl. No.: 09/809,467

(22) Filed: Mar. 15, 2001

(65) Prior Publication Data
US 2002/0130265 A1 Sep. 19, 2002

(51) Int. Cl.$^7$ ............................................. G01T 1/166
(52) U.S. Cl. .......................... 250/370.09; 250/363.04; 250/363.1
(58) Field of Search ....................... 250/370.09, 363.04, 250/363.1

(56) References Cited

U.S. PATENT DOCUMENTS

| | | | |
|---|---|---|---|
| 4,090,080 A | 5/1978 | Tosswill | 250/366 |
| 4,262,207 A | 4/1981 | Tosswill | 250/363.1 |
| 4,982,096 A | 1/1991 | Fujii | 250/367 |
| 5,075,554 A * | 12/1991 | Yunker et al. | 250/363.08 |
| 5,077,770 A | 12/1991 | Sammon | 378/101 |
| 5,967,983 A | 10/1999 | Ashburn | 600/436 |
| 5,991,357 A | 11/1999 | Marcovici | 378/19 |
| 6,046,454 A | 4/2000 | Lingren et al. | 250/370.01 |
| 6,055,450 A | 4/2000 | Ashburn | 600/431 |
| 6,091,070 A | 7/2000 | Lingren et al. | 250/370.09 |
| 6,147,353 A | 11/2000 | Gagnon et al. | 250/363.05 |
| 6,411,673 B1 * | 6/2002 | Bromberg et al. | 378/19 |

FOREIGN PATENT DOCUMENTS

| WO | WO 98/16852 | 4/1998 |
|---|---|---|
| WO | WO 02/39142 | 5/2002 |

OTHER PUBLICATIONS

G.L. Zeng, et al. "Eigen Analysis of Cone–Beam Scanning Geometries". *Three–Dimensional Image Reconstruction in Radiation and Nuclear Medicine*© 1996 by Kluwer Academic Publishers, Netherlands. Pp. 75–86.

G.L. Zeng, et al. "A cone beam tomography algorithm for orthogonal circle–and–line orbit". *Phys. Med. Biol.*, 1992, vol. 37, No. 3, 563–577.

S. Webb, et al., "Monte Carlo modelling of the performance of a rotating slit–collimator for improved planar gamma–camara imaging," *Phys. Med. Biol.*, vol. 37, No. 5, 1095–1108, 1992.

Mauderli, et al., A Computerized Rotating Laminar Radionuclide Camera, *J. Nucl. Med*, 20:341–344 (1979).

(List continued on next page.)

*Primary Examiner*—Constantine Hannaher
*Assistant Examiner*—Shun Lee
(74) *Attorney, Agent, or Firm*—Fay, Sharpe, Fagan, Minnich & McKee, LLP

(57) ABSTRACT

A subject (10) is disposed adjacent a linear detector array (18) of a nuclear camera. The subject (10) is injected with a radioactive isotope (14) and y-ray emissions indicative of nuclear decay are detected at the detector array (18) as the detector array rotates about an axis of rotation to collect data over a circular field of view. Detectors farther from the axis rotation are sampled at a higher sampling rate such that the are sampled after a generally constant arc of rotation to correct for angular aliasing. The detector array (18) rotates about the axis of rotation in a 1/sin Θ pattern with angular offset of the detector array from a longitudinal axis of the subject. This corrects for otherwise uneven sampling. A reconstruction processor (84) reconstructs the identifications of the y-ray receiving detectors, or other indicators of event detection location, and the digital peak values to generate a spherical image representation.

17 Claims, 4 Drawing Sheets

OTHER PUBLICATIONS

Entine, et al., "Cadmium Telluride Gamma Camera," *IEEE Transactions on Nuclear Science*, vol. NS–26, No. 1:552–558 (1979).

Urie, et al., "Rotating Laminar Emission Camera with GE–detector," *Med. Phys.* 8(6):865–870 (1981).

Mauderli, et al., "Rotating Laminar Emission Camera with GE–Detector: An Analysis," *Med. Phys.* 8(6):871–876 (1981).

Malm, et al., "A Germanium Laminar Emission Camera," *IEEE Transactions on Nuclear Science*, vol. NS–29, No. 1:465–468 (1982).

Mauderli, et al., "Rotating Laminar Emission Camera with GE–Detector: Further Developments," *Med. Phys.* 14(6):1027–1031 (1987).

\* cited by examiner

VARIABLE ANGULAR SAMPLING RATE FOR ROTATING SLAT-HOLE DETECTORS OF GAMMA CAMERAS

BACKGROUND OF THE INVENTION

The present invention relates to the diagnostic imaging arts. It finds particular application in conjunction with SPECT nuclear imaging systems and will be described with particular reference thereto. It will be appreciated, however, that the present invention is useful in conjunction with other systems that utilize penetrating radiation, and is not limited to the aforementioned application.

Typically in nuclear imaging, a source of radioactivity is used to provide non-invasive diagnostic images. The source is typically injected into a patient, although external sources are also utilized. Radiation from the source traverses at least a portion of the patient and is detected by radiation detectors.

Typically, a nuclear camera has one, two, or three detector heads. Each head has a large scintillator sheet, such as doped sodium iodide, which converts incident radiation photons into scintillations, i.e. flashes of light. An array of photomultiplier tubes is disposed in back of the scintillator to monitor for light flashes. The output of the photomultiplier tubes and associated circuitry indicates the coordinates of each scintillation on the sodium iodide crystal and its energy. Unfortunately, there are numerous non-uniformities and inaccuracies when using a large scintillator crystal and an array of photomultiplier tubes.

The heads have collimators disposed between the crystal and the subject to limit the trajectory along which radiation can be received. Typically, the collimators are thick lead plates with an array of apertures or bores. Radiation traveling in a trajectory through one of the bores strikes the crystal; whereas radiation traveling in other trajectories hits the collimator and is absorbed. In this manner, each scintillation defines a ray, typically perpendicular to the face of the crystal although magnifying and minifying collimators are also known. The thicker the collimator, the more accurately the ray trajectory is defined, but more radiation is absorbed in the collimator without reaching the detector.

To improve the amount of radiation that reaches the detector, it has been proposed to use collimator sheets in a single direction across a row of detectors such that detected radiation defines a plane instead of a ray. The detectors are rotated to collect the planes at many angles. For three-dimensional images, the detector was positioned at a plurality of locations around the subject and the rotating data collection process repeated. The images from the rotating data collection technique had artifacts due to non-uniformities in the data sampling.

The present invention provides a new and improved method and apparatus that overcomes the above referenced problems and others.

SUMMARY OF THE INVENTION

In accordance with one aspect of the present invention, a method of diagnostic imaging is provided. A radioactive isotope is introduced into a subject. The isotope decays and radiation indicative of nuclear decay events is detected by a rotating solid state detector array to produce planar projections. The detector is moved around the subject, gathering a plurality of different views of the subject. The detected radiation emissions are reconstructed into an image reconstruction of the subject.

In accordance with another aspect of the present invention, a diagnostic imaging apparatus is provided. A means for transmitting radiation transmits radiation that is detected by a means for detecting after passing through a portion of a subject. A first rotating means rotates the detecting means about a longitudinal axis of the subject. A second rotating means rotates the detecting means about an axis perpendicular to the longitudinal axis while the detecting means detects radiation. A means for reconstructing reconstructs the detected radiation into an image representation of the subject.

In accordance with another aspect of the present invention, a diagnostic imaging apparatus is provided. A detector array detects γ-ray emissions that pass through a portion of a subject in an imaging region. A rotation drive rotates the detector array about an axis orthogonal to the detector array. The rotation drive is mounted to a gantry for rotation about an axis of the subject. A reconstruction processor reconstructs detected γ-rays into an image representation of the subject in the imaging region.

One advantage of the present invention is that it presents a small, relatively light nuclear detector array.

Another advantage is that it presents a solid state nuclear detector array.

Another advantage is that provides uniform sampling over an imaging volume.

Another advantage is that radial resolution is conserved.

Another advantage is that angular sampling rates are conserved.

Another advantage resides in uniformly distributed data points.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT

Figure 1:
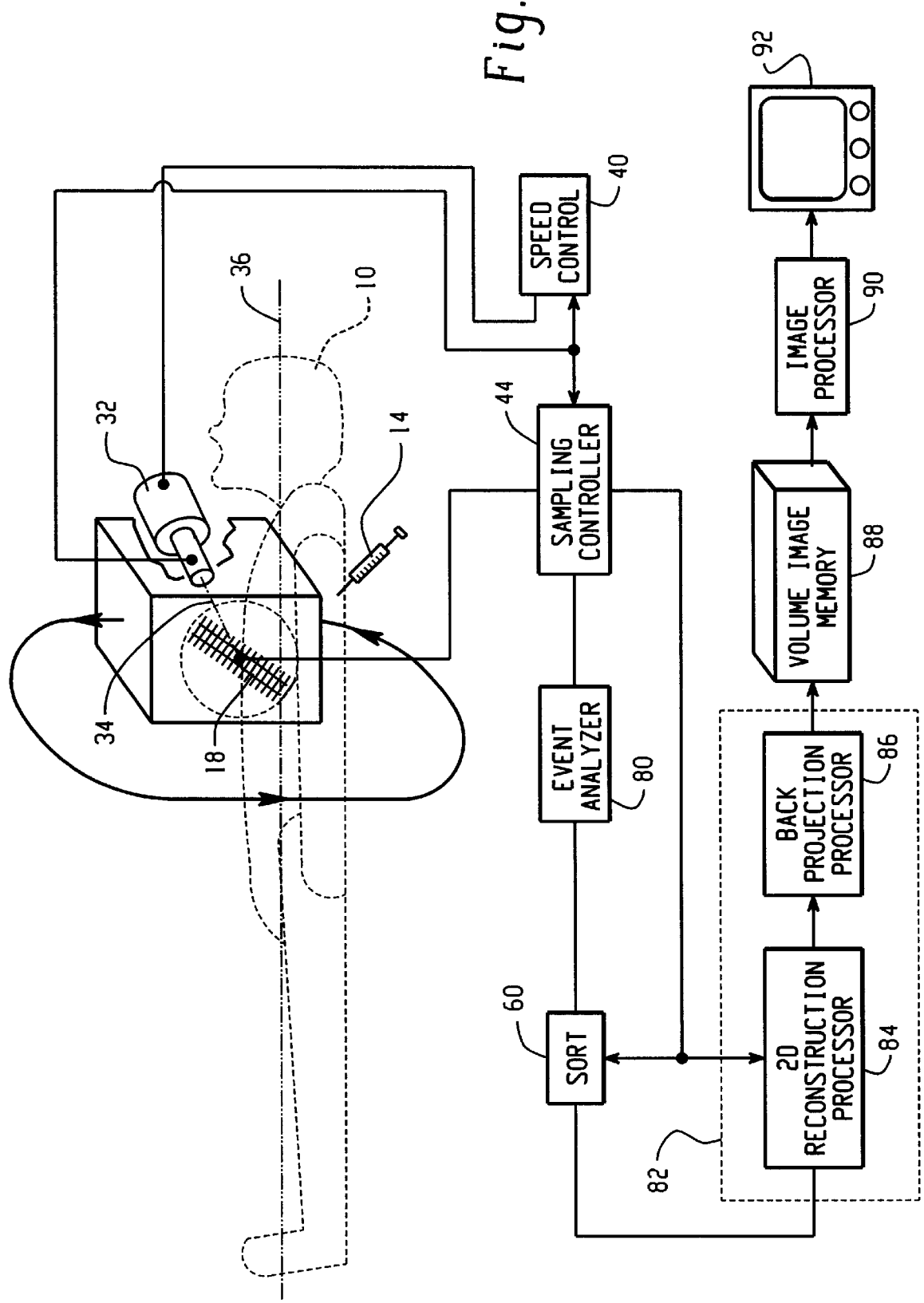
FIG. 1 is a diagrammatic illustration of a nuclear imaging device in accordance with the present invention.

With reference to FIG. 1, a region of interest of a subject 10 is disposed in an imaging region. In the preferred embodiment, a radiopharmaceutical 14 is injected into the subject, near the region to be imaged. For example, if a physician wanted to view a blockage in the aorta, the isotope would be injected into the bloodstream upstream from the blockage. As another example, the radiopharmaceutical 14 is injected into the circulatory system and its selective absorption by tissue of interest is monitored.

As quantum physics predicts, atomic nuclei of the radioactive isotope decay over time. Energy is released at the time of decay in the form of a radiation photon, more specifically, a γ-ray of characteristic energy.

Figure 2:
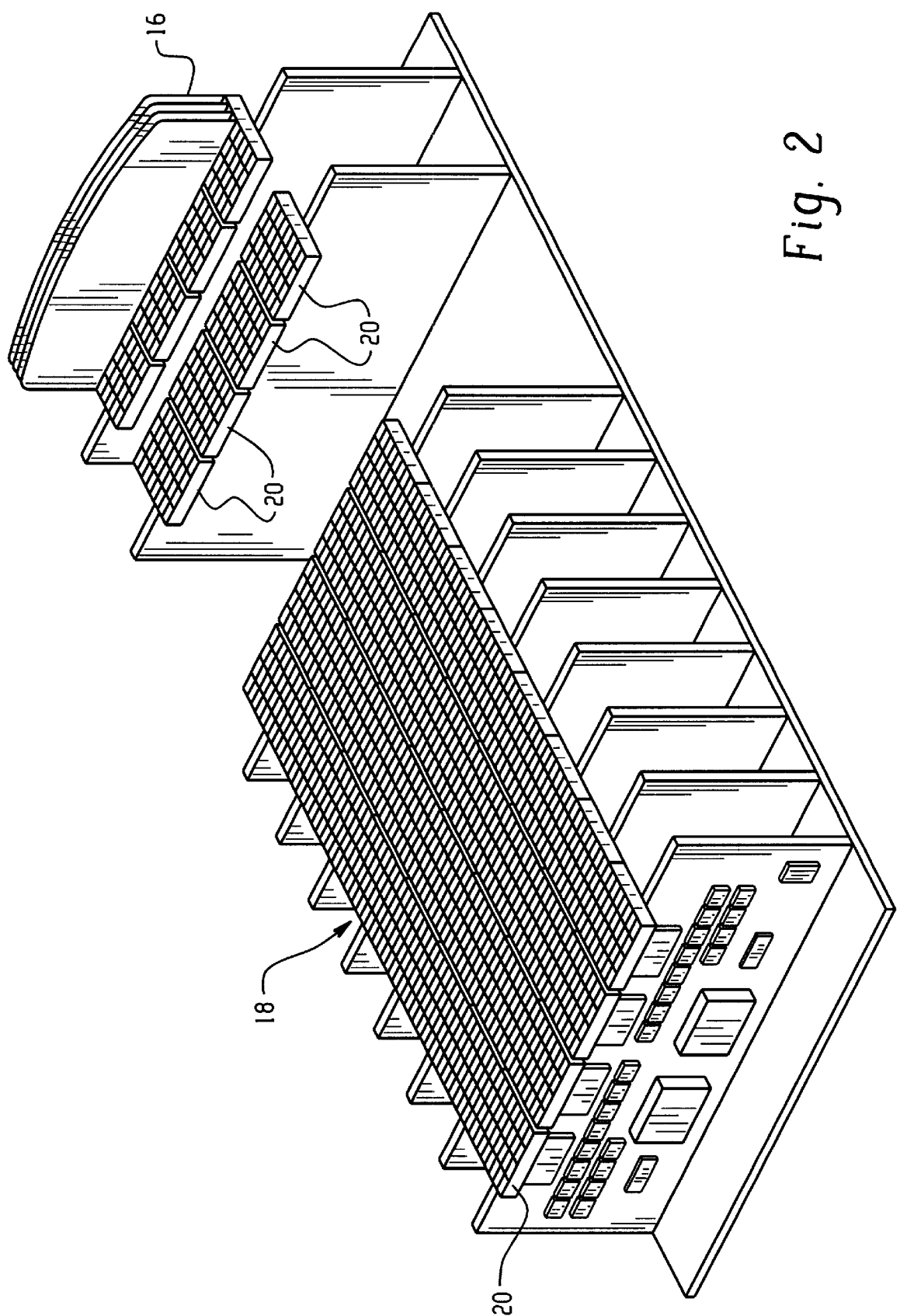
FIG. 2 is a perspective view of a detector array and collimator arrangement in accordance with the present invention.

With reference to FIG. 2, and further reference to FIG. 1, many of the γ-rays produced during an imaging process are lost, propagating in useless directions. However, some of the γ-rays pass through collimators 16, thin tungsten, lead, or other high-z vanes in the preferred embodiment, and strike a detector array 18. In the preferred embodiment and with reference to FIG. 2, the detector array 18 includes a linear array of cadmium zinc telluride (CZT) crystals. When a γ-ray strikes the detector, it frees many electrons from their bonds to the detector material. These electrons are propelled across the thickness of the crystal and form an electrical signal.

With reference to FIG. 2, the preferred embodiment of the linear detector array is defined by two dimensional detector arrays 20. The collimators 16 extend in one dimension, and the detector array 18 is treated as one-dimensional in the direction transverse to the collimator vanes for purposes of data gathering. The detectors of a single row are all sampled together as if they were a single elongated crystal for higher proton counts.

With further reference to FIG. 1, the detector array 18 is mounted on a head that is mounted to a gantry for rotation around the region of interest. In the preferred embodiment, a motor 32 rotates the detector array about a center axis 34. During rotation the detectors move through parallel to a longitudinal axis 36 of the subject 10, and 90 from the longitudinal axis 36. These two motions of the detector array 18, that is, rotation about its own center and translation of the head 30 around the subject 10, give the detector array 18 a sufficient variety of views of the subject 10 in order to reconstruct an accurate three-dimensional image representation.

The detector array 18 rotates about its own center. In the preferred embodiment, the head 30 remains stationary while the detector array 18 rotates. With parallel collimators perpendicular to the array 18, the array 18 rotates 180°. It is to be understood that this value is a minimum range of rotation, enough to obtain a full set of views. The array 18 could also perform more rotations to increase photon counts in that position and integrate the counts over a longer duration. For parallel collimators 16 other than perpendicular to the array 18, 360° of rotation is performed to obtain a full view.

Figure 3:
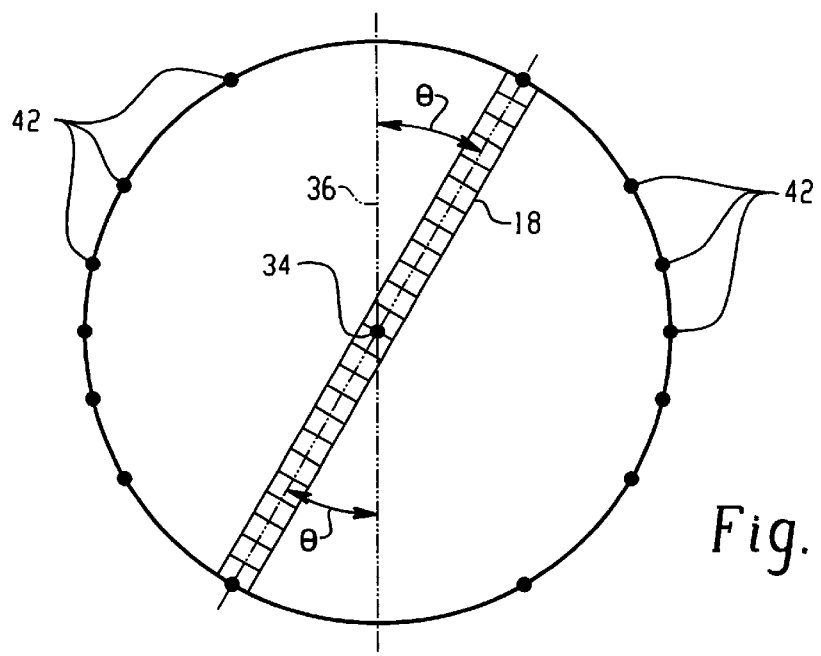
FIG. 3 a depicts rotation of the detector array about its own axis.

As the detector array 18 rotates, an outer extremity of the array traces a circle, defining the outer edge of a field of view of the detector array 18 as illustrated in FIG. 3. Indeed, all of the individual detectors 22 trace circles when rotated, but only the outermost is illustrated for clarity. In the preferred embodiment, a motor speed control 40 rotates the detector array 18 at a non-constant speed. The speed of the detector array is a function of its position relative to the longitudinal axis 36 of the patient, measured by an angle θ. More specifically to the preferred embodiment, the speed with which the detector array 18 rotates varies as a modified function of $1/\sin \theta$. The function is modified because of physical boundaries. The limit as $\theta \to 0°^+$ of $1/\sin \theta = \infty$ which would yield an infinite velocity when $\theta = 0°$. The function is also modified to take the absolute value, as the detector spins in only one direction in the preferred embodiment. Therefore, the array 18 rotates fastest when θ is closest to 0°, and slowest when θ is closest to 90°, as indicated by dots 42 in FIG. 3. A simplified manner of visualization is that the detector spends equal amounts of time moving from dot to dot in FIG. 3. In this manner, data is collected with substantially the same density at the poles as at the equator.

Figure 4:
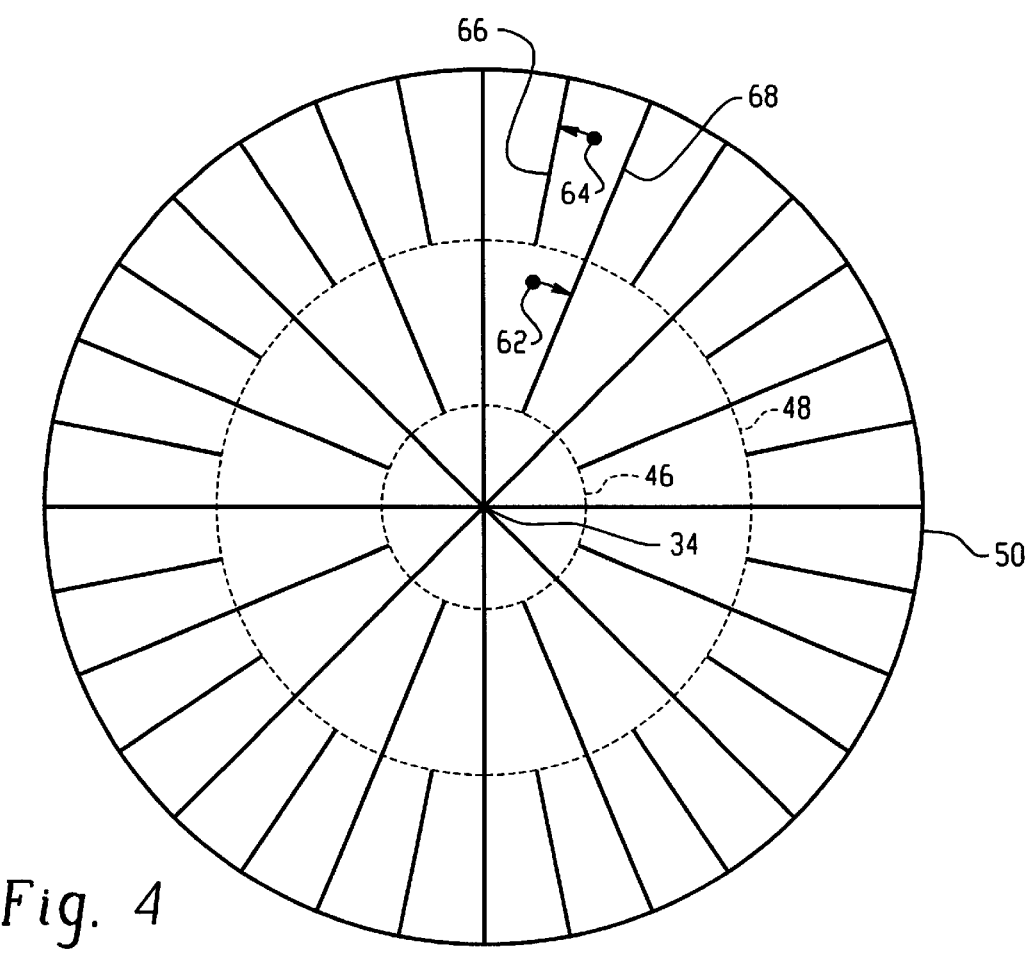
FIG. 4 depicts a data binning strategy that preserves angular sampling rates; and, FIG. 5 is a depiction of how translational motion of the detector array around an imaging volume fleshes out a field of view.

In the preferred embodiment, the detector array 18 does not stop at the points 42, but rather, rotates continuously. Data gathered by the detector array 18 is binned, that is, quantized according to the position of the array 18 at the time the data is detected as detected by a sampling controller 44. With reference to FIG. 4, it will be seen that a detector at the end of the array moves through a longer arc during each sampling period than a detector near the center. If the detectors were all sampled concurrently, there would be substantially less spatial resolution in some data than others. Accordingly, the sampling controller 44 samples the detectors with different sampling frequencies. In the illustrated embodiment, the middle third of the detectors are sampled with twice the sampling frequency as the inner third and the outer third are sampled at four times the sampling frequency. That is, there are three radial sampling regions. The first extends from the center point 34 to a circle 46. The second sampling region extends from the circle 46 to a second circle 48. The third sampling region extends from the second circle 48 to an outer periphery 50.

With reference to FIG. 4, detected data points are sorted 60 into bins according to the angle θ as discussed above, and according to radial distance from the center axis 34. For example, take points 62 and 64 and bins 66 and 68. The two points both rest on the same radius. However, the points are binned differently because of their radial distance from the center. Point 62 is sorted into bin 68 because it is in the second sampling region, whereas point 64 is in the third sampling region, and is therefore binned into bin 66. The sampling frequencies and the number of regions are selected to provide near equal resolution for all portions of the detector array.

Figure 5:
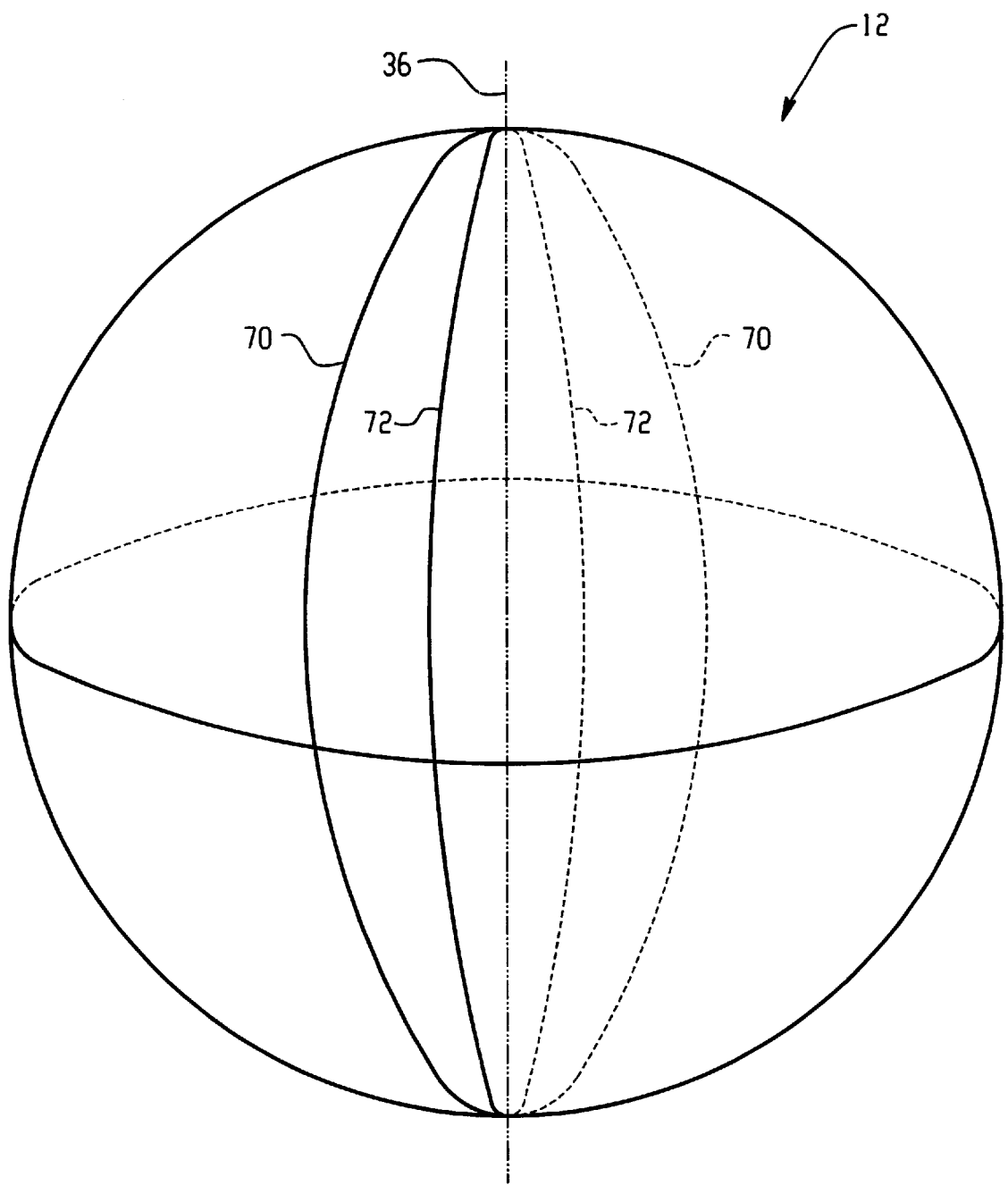

The rotational motion of the detector array 18 provides a single two-dimensional view of the imaging region 12. Multiple views from around the subject 10 are obtained to reconstruct a three-dimensional view of the spherical imaging region 12. With reference to FIG. 5, at each point around the subject 10 at which the head 30 is positioned, a two-dimensional view of the imaging region 12 is generated as discussed previously. Two of these views are illustrated in FIG. 5 by planes 70, 72.

In the preferred embodiment, movement of the array 18 around the subject 10 is in discrete steps. The array 18 stops at each step and generates a two dimensional view. Each two-dimensional view is generated using the θ dependency, discussed in conjunction with FIG. 3. The plane through the equator of the spherical volume is perpendicular to the longitudinal axis 36 and parallel to the plane of rotation of the head 30 around the subject 10. The longitudinal axis extends through the poles of the spherical volume.

With further reference to FIG. 1, an event analyzer 80 detects valid events, sorts them by energy in a dual energy study, and the like. The sorter 60 bins the valid events as explained in conjunction with FIG. 4. The events are then reconstructed into three-dimensional images by a reconstruction processor 82. In the illustrated embodiment, a two-dimensional reconstruction processor 84 reconstructs a two-dimensional projection image for each stepped position of the head 30 around the subject 10 and a backprojection processor 86 backprojects the two-dimensional images into a volumetric image memory 88 until such time that an operator wishes to view them. Upon such a demand, an image processor 90 processes selected portions of the volumetric image for display on a human-readable display 92 such as a computer monitor, LCD display, active matrix monitor, or the like.

In an alternate embodiment, the detector array 18 is rotated at a temporally constant speed, spending an equal amount of time at all locations.

In another alternate embodiment, the head 30 moves continuously about the subject 10.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A method of diagnostic imaging comprising:
   a) introducing a radioactive isotope into a subject located in an imaging region;
   b) continuously rotating a solid state detector array within a detector head about an axis perpendicular to a longitudinal axis of the subject while detecting photon emissions indicative of nuclear decay to generate a plurality of planar projections of an examination region each at a plurality of angular orientations;
   c) rotating the detector head around the longitudinal axis of the subject while continuing the continuous rotating and detecting of step (b);
   d) binning detected radiation events detected by the detector array into bins in accordance with a distance of the detectors from the detector axis, the bins corresponding to arc segments of the rotation of the detector array around the detector axis, with the bins corresponding to arc segments of different size in accordance with the distance from the detector axis; and,
   e) reconstructing the detected photon emissions into an image representation of the subject in the imaging region.

2. A method of diagnostic imaging comprising:
   a) introducing a radioactive isotope into a subject located in an imaging region;
   b) rotating a solid state detector array about a detector axis which is perpendicular to the array while sampling detectors of the array at non-uniform sampling frequencies for photon emissions indicative of nuclear decay to generate a plurality of planar projections of an examination region each at a plurality of angularly rotated orientations;
   c) moving the detector array around a longitudinal axis of the subject while continuing the step detecting with the rotating array at a plurality of of rotating about the axis perpendicular to the array and orientations around the longitudinal axis;
   d) reconstructing the detected photon emissions into an image representation of a distribution of the radio isotope in the subject.

3. The method as set forth in claim 2, wherein the step of rotating includes:
   rotating the detector array continuously about a center point.

4. The method as set forth in claim 2, further including separating detected photons into discrete detection bins that most closely correspond to an actual position of the detector array.

5. The method as set forth in claim 2, wherein the detector array is moved around the longitudinal axis in lateral steps and wherein the reconstructing step includes:
   at each lateral step reconstructing the detected photon emissions into a circular projection image; and
   backprojecting the circular projection images to generate a spherical volume image.

6. A method of diagnostic imaging comprising:
   a) introducing a radioactive isotope into a subject located in an imaging region;
   b) rotating a solid state detector array about a detector axis which is perpendicular to an input face of the array while detecting photon emissions indicative of nuclear decay;
   c) sampling detectors of the array close to the detector axis at a lower sampling rate than detectors further from the axis of array rotation to generate a plurality of projections of an examination region each at a plurality of angular orientations;
   d) moving the detector array around the imaging region while continuing steps in) and a);
   e) reconstructing the detected photon emissions into an image representation.

7. The method as set forth in claim 6, wherein the rotating step includes:
   rotating the detector array at a non-constant velocity.

8. The method as set forth in claim 7, wherein the detector array rotates faster when it is near parallel to a longitudinal axis of the imaging region and slower when it is near perpendicular to the longitudinal axis.

9. A method of diagnostic
   a) moving a solid-state detector array around a longitudinal axis of an imaging region;
   b) while the detector array is moved around the longitudinal axis of the imaging region, rotating the solid state detector array about a detector rotation axis perpendicular to the array faster as a detector longitudinal axis of the detector becomes closer to parallel with the longitudinal axis of the imaging region;
   c) rotating the detector slower as the detector longitudinal axis becomes closer to 90° from parallel with the longitudinal axis of the imaging region;
   d) detecting photon emissions indicative of nuclear decay to generate a plurality of planar projections of an examination region each at a plurality of angular orientations;
   e) reconstructing the detected photon emissions into an image representation.

10. The method as set forth in claim 9, wherein the detector is rotated as a function of an inverse sine of an angle of the detector longitudinal axis with the longitudinal axis of the imaging region.

11. The method as set forth in claim 10, further including;
    sampling detectors off the array which are farther from the detector rotation axis more often than detectors which are closer to the detector rotation axis.

12. A diagnostic imaging apparatus comprising;
    a detector array for detecting the radiation from an imaging region;
    a first rotating means for rotating the detecting array around a longitudinal axis of the imaging region;
    a second rotating means for continuously rotating the detecting array about a detector axis perpendicular to the longitudinal axis while the first rotating means rotates the detector array around the longitudinal axis;

a binning means for binning detected radiation events detected by detectors of the array into bins in accordance with a distance of the detectors from the detector axis, the bins corresponding to arc segments of the rotation of the detector array around the detector axis, with the bins corresponding to arc segments of different size in accordance with the distance from the detector axis; and, a means for reconstructing the detected radiation events into an image representation.

13. The diagnostic imaging apparatus as set forth in claim 12, wherein the detector array includes a linear array of individual crystal detectors.

14. A diagnostic imaging apparatus comprising:

a means for transmitting radiation one of from and through a subject in an imagining region;

a means for detecting the radiation after its transmission through at least a portion of the subject;

a first rotating means for rotating the detecting means about a longitudinal axis of the imaging region;

a second rotating means for continuously rotating the detecting means about a detector axis perpendicular to the imaging region longitudinal axis while the detecting mean detects radiation; is a sampling means for controlling sampling of the detecting means in accordance with a distance of radiation detection from the detector rotation axis; and, a reconstructing means that generates a volume image of the subject from the radiation detected by the detecting means.

15. A diagnostic imaging apparatus comprising:

a means for transmitting radiation one of from and through a subject in an imaging region;

a means for detecting the radiation after its transmission through at least a portion of the subject;

a first rotating means for rotating the detecting means about a longitudinal axis of the imaging region;

a second rotating means for rotating the detecting means about a detector axis perpendicular to the imaging region longitudinal axis while the detecting means detects radiation;

a means for controlling the second rotating means to varying the speed of rotating in accordance with a rotation angle of the detecting means; and, a reconstructing means that generates a volume image of the subject from the radiation detected by the detecting means.

16. A diagnostic imaging apparatus including:

a detector array for detecting y-ray emissions from an imaging region;

a rotational drive connected with the detector array to rotate the detector array about a detector array drive axis orthogonal to a face of the detector array, the detector array and the rotational drive being mounted to a gantry for rotation about a gantry axis of rotation;

a sampling controller which controls a rate at which detectors of the detector array are sampled, detectors further from the drive axis being sampled more frequently than detectors closer to the drive axis;

a reconstruction processor that reconstructs the is detected y-rays into an image representation.

17. A diagnostic imaging apparatus comprising:

a detector head mounted for rotation about a longitudinal axis of an imaging region;

a detector array mounted in the detector head for detecting y-ray emissions from the imaging region;

a rotational drive connected with the detector array to rotate the detector array within the detector head about a drive axis;

a drive controller which varies a rotation speed at which the rotational drive rotates the detector array in accordance with angular position of the detector array relative to the longitudinal axis;

a reconstruction processor that reconstructs the detected y-rays into an image representation of the subject in the imaging region.

\* \* \* \* \*